(12) United States Patent
Freudenberger

(10) Patent No.: US 10,952,869 B2
(45) Date of Patent: Mar. 23, 2021

(54) INTERBODY FUSION CAGES

(71) Applicant: Mobarn Medical Devices, LLC, New Orleans, LA (US)

(72) Inventor: Curt Freudenberger, Huntsville, AL (US)

( * ) Notice: Subject to any disclaimer, the term of this patent is extended or adjusted under 35 U.S.C. 154(b) by 208 days.

(21) Appl. No.: 16/304,430

(22) PCT Filed: May 27, 2017

(86) PCT No.: PCT/US2017/034883
§ 371 (c)(1),
(2) Date: Nov. 26, 2018

(87) PCT Pub. No.: WO2017/205863
PCT Pub. Date: Nov. 30, 2017

(65) Prior Publication Data
US 2019/0142606 A1    May 16, 2019

Related U.S. Application Data

(60) Provisional application No. 62/342,572, filed on May 27, 2016.

(51) Int. Cl.
*A61F 2/44* (2006.01)
*A61F 2/30* (2006.01)
*A61F 2/28* (2006.01)

(52) U.S. Cl.
CPC .............. *A61F 2/4465* (2013.01); *A61F 2/28* (2013.01); *A61F 2/2846* (2013.01); *A61F 2/30744* (2013.01); *A61F 2/4455* (2013.01); *A61F 2002/305* (2013.01); *A61F 2002/3093* (2013.01); *A61F 2002/30179* (2013.01); *A61F 2002/30405* (2013.01); *A61F 2002/30578* (2013.01); *A61F 2002/30593* (2013.01); *A61F 2002/30904* (2013.01); *A61F 2310/00023* (2013.01); *A61F 2310/00029* (2013.01); *A61F 2310/00359* (2013.01); *A61F 2310/00407* (2013.01); *A61F 2310/00413* (2013.01)

(58) Field of Classification Search
CPC .............................. A61F 2/447; A61F 2/4465
See application file for complete search history.

(56) References Cited

U.S. PATENT DOCUMENTS

| 7,794,500 B2 * | 9/2010 | Felix ................. A61F 2/447 623/17.11 |
| 2004/0117020 A1 * | 6/2004 | Frey ................. A61F 2/4611 623/17.11 |

(Continued)

*Primary Examiner* — Andrew Yang

(57) ABSTRACT

An implant for interbody fusion of vertebrae comprising a unibody cage structure having an enveloping cage volume and a minimized material volume. The cage structure comprises a first and a second generally planar ring member, each ring member formed from an opposing pair of lengthwise joists and an opposing pair of cross joists, the joists together forming a large opening through the ring member. The ring members are fixedly sandwiched on a plurality of support members, the support members holding the ring members in a spaced apart relationship to thereby provide a large void volume relative to the enveloping cage volume, to thereby allow for receipt of a large volume of bone graft within the cage structure.

5 Claims, 15 Drawing Sheets

(56) References Cited

U.S. PATENT DOCUMENTS

| | | | |
|---|---|---|---|
| 2012/0158144 A1* | 6/2012 | Ullrich, Jr. | A61F 2/4465 623/17.16 |
| 2016/0113773 A1* | 4/2016 | Ganem | A61F 2/447 623/17.16 |
| 2016/0324653 A1* | 11/2016 | Flickinger | A61F 2/30771 |

* cited by examiner

INTERBODY FUSION CAGES

CROSS REFERENCE TO RELATED APPLICATIONS

This application is a 35 USC § 371 of PCT/US2017/034883 filed May 27, 2017, which is pending; PCT/US2017/034883 claims priority to U.S. Provisional Patent Application 62/342,572, filed May 27, 2016. This application claims the benefit of and incorporates by reference all of the above cited applications.

STATEMENT REGARDING FEDERALLY SPONSORED RESEARCH

Not applicable

FIELD OF THE INVENTION

The present invention relates to spinal implants, and more particularly to lumbar and anterior cervical discectomy fusion cages configured to receive bone graft.

BACKGROUND OF THE INVENTION

Various implants have been developed for use in lumbar interbody fusion (LIF) and anterior cervical discectomy fusion (ACDF), including cages. Current LIF and ACDF cages emphasize structural support over openness, which decreases options for the use of interbody graft to enhance fixation and fusion. There is a need for interbody fusion cages that overcome the shortcomings of the prior art. The present invention is directed primarily to improved fusion cage implants for transforaminal lumbar interbody fusion (TLIF), direct lateral lumbar interbody fusion (DLIF), anterior lumbar interbody fusion (ALIF), and anterior cervical discectomy fusion (ACDF), together with methods of use and of manufacture of such implants.

OBJECTS AND SUMMARY OF THE INVENTION

It is an object of the inventions to provide improved spinal implants for use in lumbar interbody fusion ("LIF").

It is an object of the inventions to provide LIF cages that provide sufficient structural support for LIF procedures while also featuring large internal void volumes communicating with large external openings, the larger volumes and openings relative to structure providing increased options for using interbody graft to enhance fixation and fusion.

One object of the inventions is to provide a TUT cage that can be readily inserted transforaminally and which provides a large void volume and external openings for use with interbody graft.

Another object of the inventions is to provide a DLIF cage that can be affixed to selected lateral portions of the lumbar region.

Another object of the inventions is to provide an ALIF cage that includes a removable clip for containing graft.

Another object of the inventions is to provide anterior cervical discectomy fusion cages having the characteristics described herein.

The foregoing objectives are achieved by providing LIF and cervical cages having the features described herein.

Embodiments of the invention include an implant device for interbody fusion of lumbar or cervical vertebrae comprising a unibody cage structure having an enveloping cage volume and a minimized material volume. The cage structure comprises a first and a second generally planar ring member, each ring member formed from an opposing pair of lengthwise joists and an opposing pair of cross joists, the joists together forming a large opening through the ring member. The ring members are fixedly sandwiched on a plurality of support members, the support members holding the ring members in a spaced apart relationship to thereby provide a large void volume relative to the enveloping cage volume, to thereby allow for receipt of a large volume of bone graft within the cage structure.

A ratio of the void volume to the enveloping cage volume may be between about 0.7 to about 0.9. The ratio of the void volume to the enveloping cage volume may be between about 0.79 to about 0.85. A ratio of the void volume to the material volume may be between about 3.8 to about 6.0.

In embodiments, the ring members are positioned on opposing lateral sides of the cage, such that one of the lengthwise joists of each ring member serves as a superior loading surface, the other of the lengthwise joists of each ring member serves as an inferior loading surface, and the cross joists are configured to distribute load between opposing lengthwise joists. The cross joists may be curved, such that each ring member has a substantially race-track configuration. The cage may further comprise at least one substantially vertical strut sandwiched between the opposing lengthwise joists of each ring member to further distribute load. The at least one substantially vertical strut may comprise a pair of substantially vertical struts.

In embodiments, the support members may comprise a base member on a posterior end of the ring members and an arrangement of arcuate struts on an anterior end of the ring members. The arrangement of arcuate struts may have an X-shape.

In embodiments, the device is configured for use as a transforaminal lumbar interbody fusion (TLIF) cage. In TLIF embodiments, the ratio of the void volume to the enveloping cage volume may be between about 0.79 to about 0.81. A ratio of the void volume to the material volume is between about 3.9 to about 4.1. The joists may be between about 1.5 to about 2.5 mm in diameter. Each of the vertical struts may have an outer diameter of between about 1.5 mm to about 2.5 mm.

In other embodiments, the first ring member is on a superior side of the cage and serves as a superior loading surface, the second ring member is on an inferior side of the cage and serves as an inferior loading surface, and the support members are a plurality of substantially vertical struts positioned and configured to distribute load between the ring members. The plurality of substantially vertical struts may include four corner struts, with each of the corner struts positioned substantially at an intersection between the lengthwise joists and the cross joists. A pair of the corner struts may be taller than an opposing pair of the corner struts, to thereby provide the cage structure with a lordosis angle. The lordosis angle may be between about 6 and about 20 degrees, such as between about 8 to about 12 degrees. At least one of the lengthwise joists may be arcuate. The first and second ring members may be substantially mirror images of one another.

In embodiments, the device may be sized and configured for use as a direct lateral lumbar interbody fusion (DLIF) cage. The plurality of substantially vertical struts may further include a pair of internal struts, each of the internal struts substantially centered between the lengthwise joists on opposing sides of the cage to thereby distribute load between the lengthwise joists. In DLIF embodiments, the ratio of the void volume to the enveloping cage volume may be between about 0.84 to about 0.86. A ratio of the void volume to the material volume may be between about 5.6 to about 5.8. The joists may be about 4 mm wide and 1.5 mm thick. Each of the vertical struts may have an outer diameter of about 4 mm.

In embodiments, the device is sized and configured for use as an anterior lumbar interbody fusion (ALIF) cage. In ALIF embodiments, the ratio of the void volume to the enveloping cage volume may be between about 0.83 to about 0.85. A ratio of the void volume to the material volume may be between about 5.1 to about 5.2. The may be about 4 mm wide and about 1.5 mm thick. The vertical struts may have an outer diameter of about 4 mm. A clip-on side cap member may be provided, the side cap member configured to removably attach to the vertical strut members to thereby assist in containing bone graft within the cage.

In embodiments, the device is sized and configured for use as an anterior cervical discectomy fusion (ACDF) cage. In ACDF embodiments, the ratio of the void volume to the enveloping cage volume may be between about 0.81 to about 0.83. A ratio of the void volume to the material volume may be between about 4.68 to about 4.70. The joists are about 2.5 mm wide and about 0.75 mm thick. The vertical struts may have an outer diameter of about 2.5 mm.

Methods of fusing adjacent posterior and anterior lumbar or cervical vertebrae of a patient are provided, such as providing an implant device as described herein, inserting the implant between adjacent vertebrae of said patient, and inserting a bone graft in the void volume of the implant.

The foregoing and other objects, features, aspects and advantages of the invention will become more apparent from the following detailed description of the invention when considered in conjunction with the accompanying drawings.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

The inventions will be defined partly with respect to certain volumes and ratios. As used for the various cage embodiments described herein, "enveloping volume" means the volume of a rectangular box tightly surrounding the outermost edges of the cage. "Net enveloping volume" means "enveloping volume" minus the triangular wedge area that is not occupied by the cage due to the presence of a lordosis angle (one side higher than the other). As such, enveloping volume has a slightly large volume than net enveloping volume. "Material volume" (sometimes referred to as "structural volume") means the volume occupied by the physical structure of the cages (struts, joists, etc.). "Void volume" means enveloping volume minus material volume. "Net void volume" means net enveloping volume minus material volume. Thus, it will be appreciated that enveloping volume includes both the material volume and the void volume, while net enveloping volume includes both the material volume and the net void volume. From these volumetric aspects, certain ratios can be determined; these ratios are important to the function and concept of the inventions described herein, as will be described below.

TLIF Cage

Figure 29:
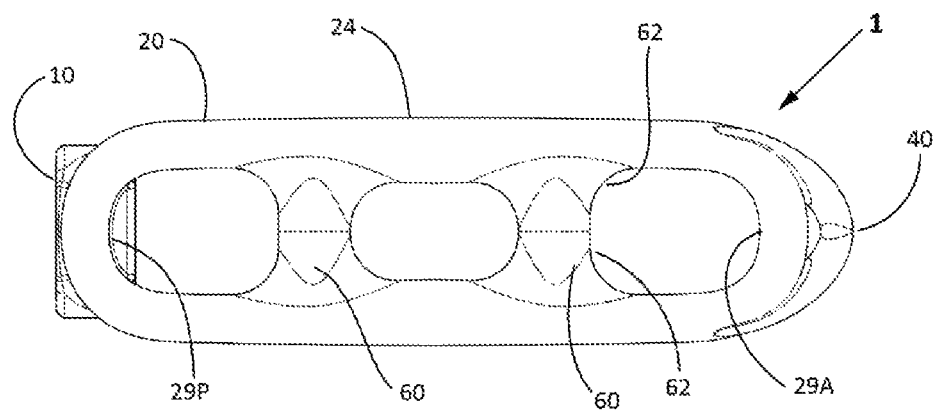
FIG. 29 is a side view of one embodiment of a TLIF cage of the invention.

FIGS. 29-34 show an embodiment of a TLIF cage 1. As shown in the view of FIG. 29, the TLIF cage 1 generally comprises a unibody frame structure having a posterior base 10, an anterior end 40, a plurality of lengthwise joist structures 20 extending between the posterior base 10 and the anterior end 40, and an open area or void volume 50 formed internal to the posterior base 10, the joist structures 20, and the anterior end 40.

Figure 30:
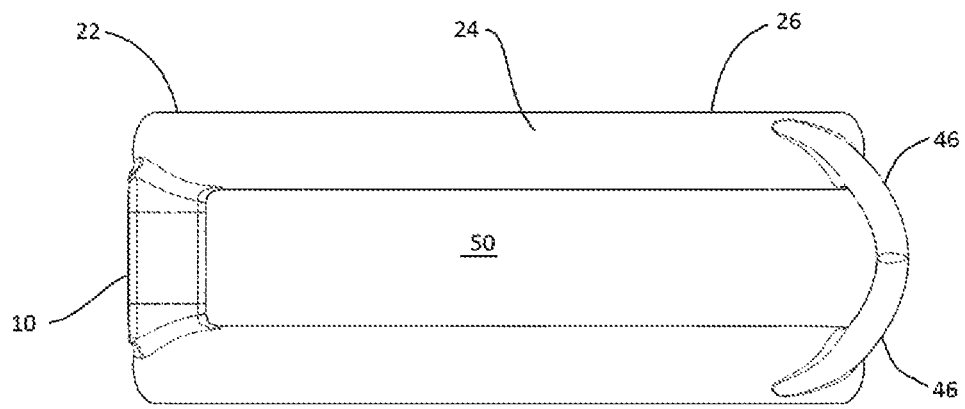
FIG. 30 is a side view of one embodiment of a TLIF cage of the invention.
Figure 31:
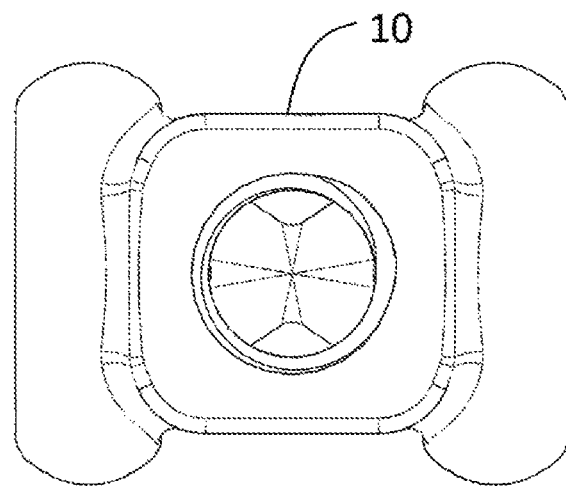
FIG. 31 is a rear view of one embodiment of a TLIF cage of the invention.

In the side view of FIG. 29, it can be seen that joist structures 20 are provided by a pair of opposing unibody load-bearing ring members 21. Each ring member 21 is elongated into an oval or racetrack shape having opposing lengthwise portions 20. As indicated in FIG. 30, each joist structure 20 includes a posterior support section 22, an anterior support section 26, and a lengthwise joist section 24 formed between the posterior and anterior support sections 22, 26. Ends of the posterior and anterior support sections 22, 26 merge into a curved or arcuate configuration to thereby form the ring members 21. The unibody, opposingly curved configuration of the ring members 21 helps support the load of opposing vertebrae on the lengthwise joist sections 24. As can be observed in FIGS. 29-34, the ring members 21 are preferably annular in cross-section, such that each ring member 21 has a tubular appearance, to further increase the strength of the ring member 21 and particularly the joist sections 24 of the ring members 21.

To further strengthen the lengthwise joist sections 24, one or more struts 60 may be provided between the lengthwise joist sections 24. In the embodiment of FIGS. 29-34, a pair of struts 60 is provided on each ring member 21 between each pair of lengthwise joist sections 24. For further strength, the ends each strut 60 can be formed as a curved or actuate section 62 that merges into the adjacent joist 24.

Figure 32:
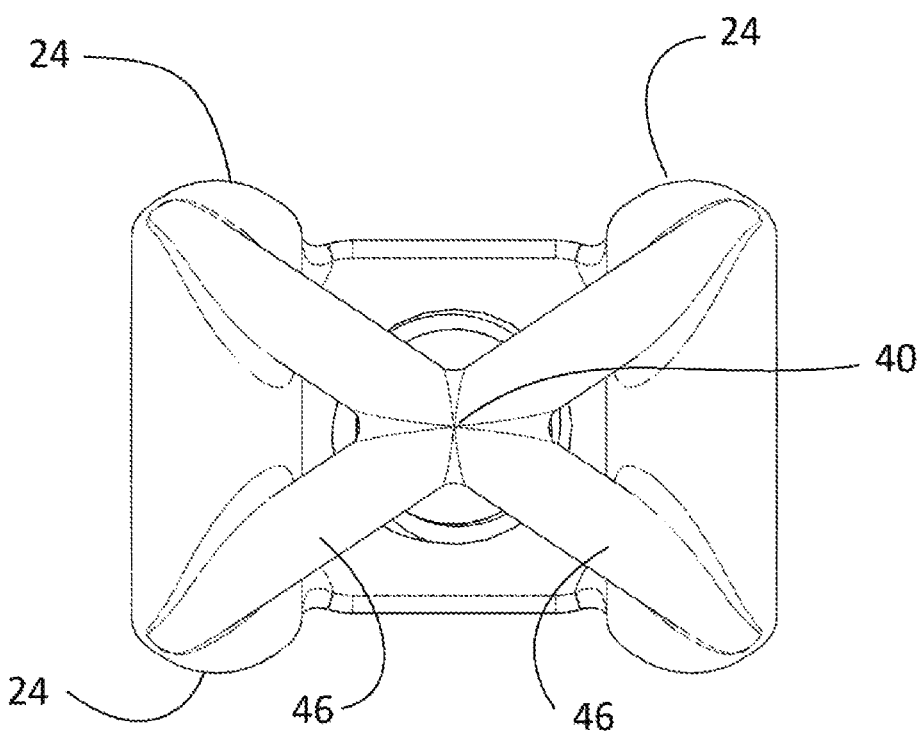
FIG. 32 is a front view of one embodiment of a TLIF cage of the invention.
Figure 33:
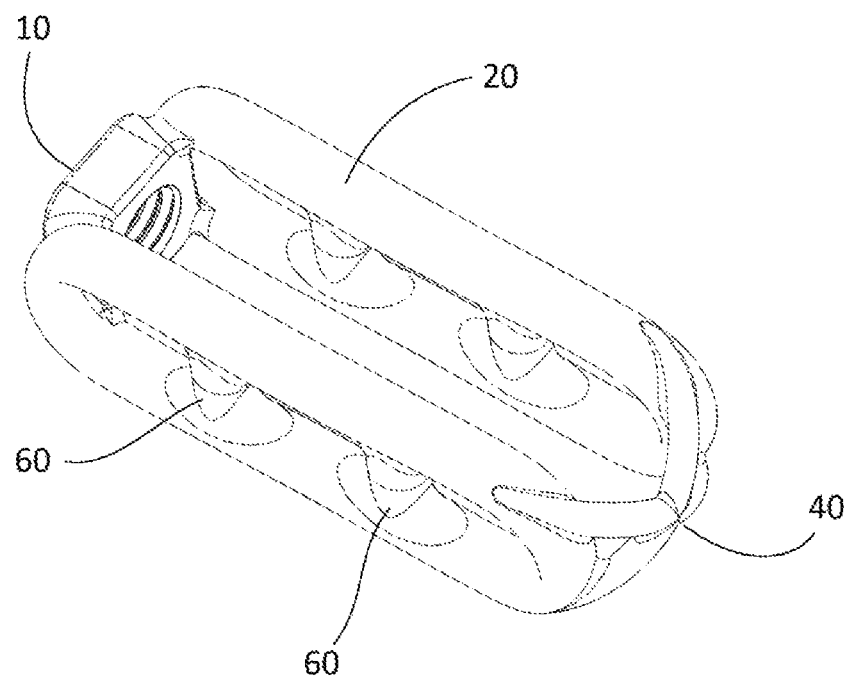
FIG. 33 is a front-side isometric view of one embodiment of a TLIF cage of the invention.
Figure 34:
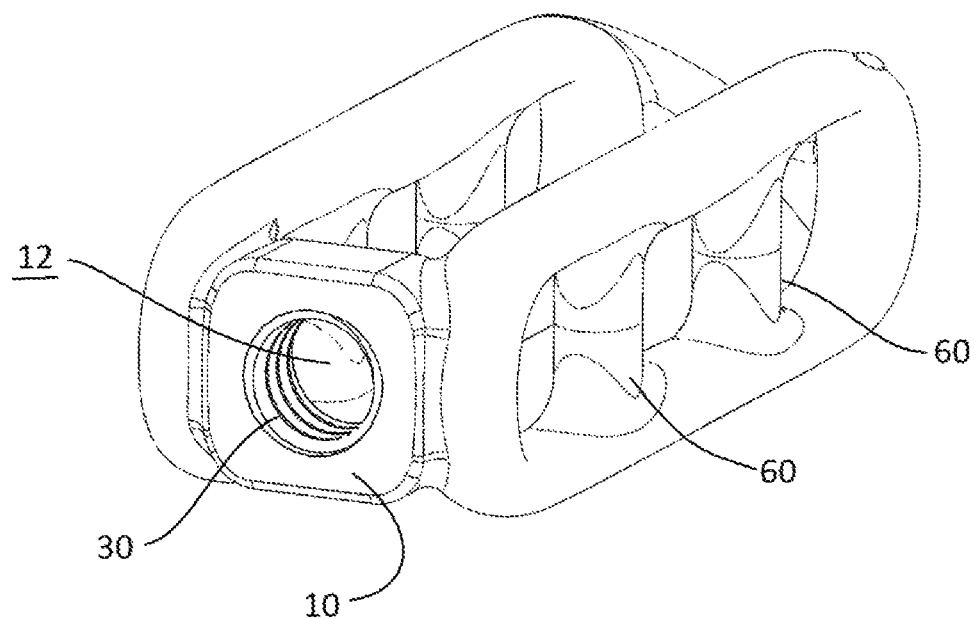
FIG. 34 is a rear-side isometric view of one embodiment of a TLIF cage of the invention.
Figure 35:
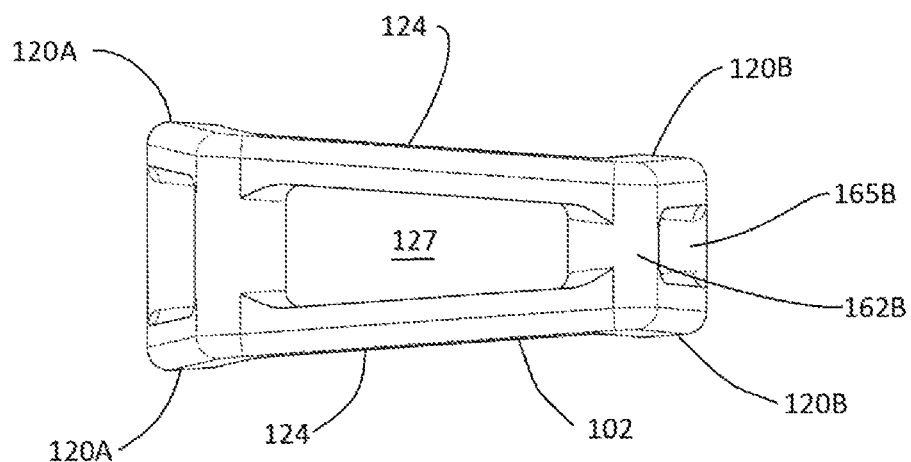
FIG. 35 is a side view of one embodiment of a DLIF cage of the invention.

As can be seen in FIGS. 30 and 32, the anterior support sections 26 of the ring members 21 are fixed in a spaced apart arrangement via a plurality of struts 46 at the anterior end 40 of the cage 1. The anterior end 40 of the cage 1 is formed by a merger of the anterior struts 46. When viewed from the lateral view of FIG. 30 or the superior/inferior view of FIG. 33, the opposing struts 46 form a generally U-shaped configuration, which further contributes to the strength of the cage 1.

As shown in FIG. 30, the posterior support sections 22 of the ring structures 21 are contiguously formed with the posterior base 10, to provide a unibody structure. In this manner, the posterior base 10 serves, along with the struts 46 described above, to hold the opposing ring structures 21 in a rigid spaced arrangement. In one preferred embodiment shown in FIG. 2, the posterior support sections 22 extend from approximately a middle or mid-portion of the posterior base 10. The features of the posterior base 10 are similar to those described above with reference to FIGS. 1-6, including an internally threaded 30 screw hole 12. However, it will be noted that the posterior base 10 of the embodiment of FIGS. 29-34 can be made shorter, due to the additional strength features, thus freeing up some space for greater void volume.

In one embodiment, each of the TLIF cage 1 is preferably about 25 mm in length, from the posterior base 10 to the anterior end 40. The width of the cage 1 is about 9.5 mm, such as about 8.5 mm to about 10.5 mm. The height of the cage 1 is between about 7 to about 14 mm, such as about 10 mm. The joists of the ring members 21 have a major diameter of about 2.5 mm and a minor diameter about 1.5. The major diameter is preferably centered on the joist 24 in order to maximize loading bearing.

As may be appreciated from the foregoing description, some of the improved characteristics of the TLIF cage 1 include a minimized volume, a reduced cross-sectional area yet with support strength comparable to a conventional TLIF cage, and a maximized internal void volume 50. The void volume 50 enables use of higher amounts of bone graft in the internal void volume 50. In embodiments, the overall or enveloping volume of the TLIF cage 1 is between about 2000 $mm^3$ to about 2800 $mm^3$, such as about 2375 $mm^3$. The volume of the TLIF cage structure, or material volume, is between about 400 $mm^3$ to 600 $mm^3$, such as about 481 $mm^3$; and the TLIF void volume 50 is between about 1,700 $mm^3$ to about 2,100 $mm^3$, such as about 1,894 $mm^3$. The ratio of the void volume 50 to the overall cage volume may be between about 0.75 and about 0.85, such as about 0.80, or 80%. The ratio of the void volume 50 to the material volume of the TLIF cage structure is preferably between about 3.7 to about 4.3, such as about 4.0. These void volume ratios are much higher than the ratios found in conventional TLIF cages, and provide the advantages discussed herein.

FIGS. 1-6 show an alternative embodiment of a TLIF cage 1. As shown in the oblique view of FIG. 6, the TLIF cage 1 generally comprises a unibody frame structure having a posterior base 10, an anterior end 40, a plurality of joist structures 20 extending between the posterior base 10 and the anterior end 40, and an open area or void volume 50 formed internal to the posterior base 10, the joist structures 20, and the anterior end 40.

Figure 1:
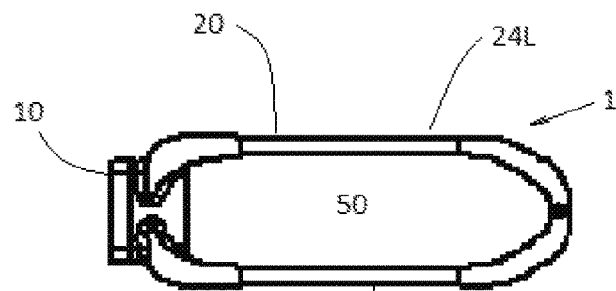
FIG. 1 is a side view of one embodiment of a TLIF cage of the invention.
Figure 3:
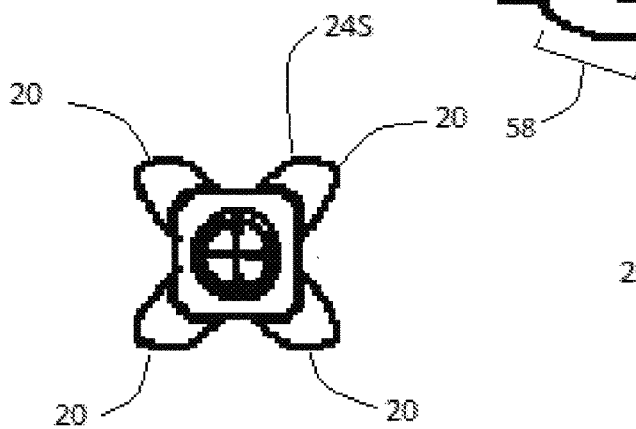
FIG. 3 is a rear view of one embodiment of a TLIF cage of the invention.

As shown in FIG. 1, the posterior base 10 is preferably cube shaped, although other shapes could be used. The sides of the cube are preferably about 7 mm in length. As shown in FIG. 3, a screw hole 12 is formed in the posterior base 10. The screw hole 12 is preferably about 3.5 mm in diameter. The screw hole 12 is internally threaded 30 for receipt of a fixation screw or a threaded end of an insertion device. The internal thread 30 may be a machine thread. In one embodiment, the insertion device is a lengthwise device (not shown) having a handle on one end and a cage engagement end on an opposing end, the cage engagement end featuring two or more tines spaced to engage matching apertures on the posterior base 10, the tines serving to stabilize the insertion device on the cage 1 during insertion of a screw through the cage engagement end and into the screw hole 12 to thereby removably secure the insertion device on the cage 1.

Figure 2:
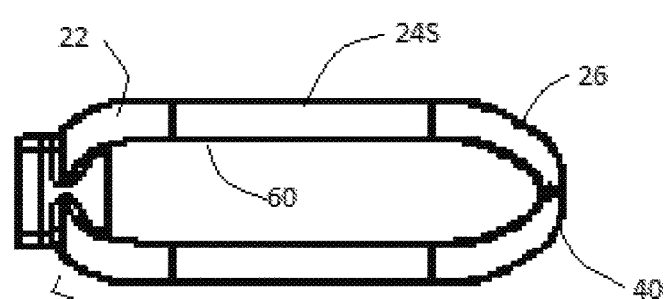
FIG. 2 is a top view of one embodiment of a TLIF cage of the invention.

As indicated in FIG. 2, each joist structure 20 includes a posterior support section 22, an anterior support section 26, and a lengthwise joist section 24 formed between the posterior and anterior support sections 22, 26. Each of the posterior and anterior support sections 22, 26 has a curved or arcuate configuration to help support the load of opposing vertebrae on the lengthwise joist sections 24.

Figure 4:
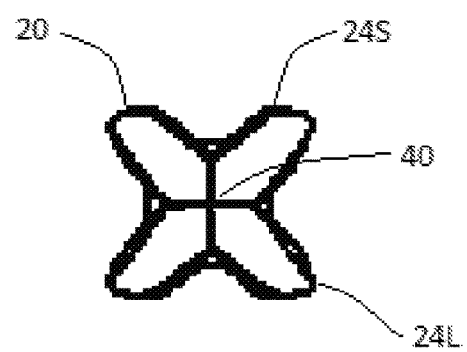
FIG. 4 is a front view of one embodiment of a TLIF cage of the invention.
Figure 5:
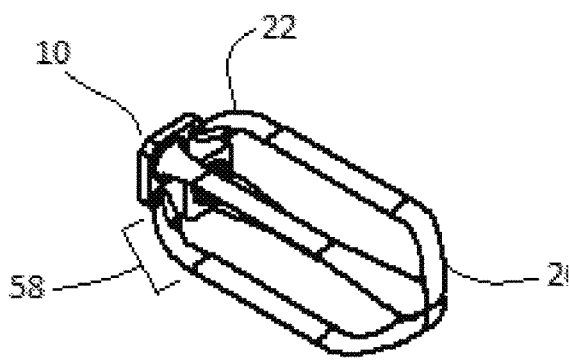
FIG. 5 is a front-side isometric view of one embodiment of a TLIF cage of the invention.
Figure 6:
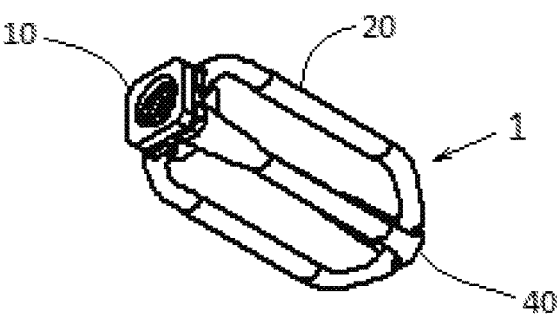
FIG. 6 is a rear-side isometric view of one embodiment of a TLIF cage of the invention.
Figure 7:
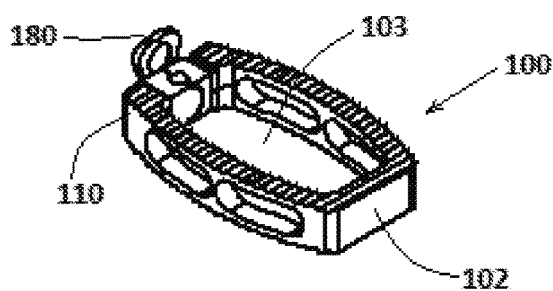
FIG. 7 is a top side isometric view of one embodiment of a DLIF cage of the invention showing a rotational plate in an attachment orientation.

As can be seen in the posterior view of FIG. 3 and the anterior view of FIG. 4, the four joist structures 20 can be characterized as axially arranged or aligned around a longitudinal axis of the cage 1. As shown in FIGS. 1-3, the posterior support sections 22 of the joist structures 20 extend from the posterior base 10. The posterior support sections 22 are contiguously formed with the posterior base 10, to provide a unibody structure. In one preferred embodiment shown in FIG. 2, the posterior support sections 22 extend from approximately a middle or mid-portion of the posterior base 10.

As can be seen in FIG. 4, the anterior support sections 26 of the joist structures merge at the anterior end 40 of the cage 1. Thus, the anterior end 40 of the cage 1 is formed by a merger of anterior support sections 26. When viewed from the lateral view of FIG. 1 or the superior/inferior view of FIG. 2, the opposing anterior support sections 26 of the joist structures 20 form a generally U-shaped configuration, which contributes to the strength of the cage 1.

As indicated in FIGS. 1-2, some or all of the lengthwise sections 24 of each of the joist structures 20 preferably have a somewhat pancaked profile, with differing superior/inferior and lateral dimensions. When viewed superiorly or inferiorly, as shown in FIG. 2, the support side 24S of the lengthwise section 24 has a wide dimension. This wide dimension of the support side 24S allows for loading on a vertebral body surface and also provides greater surface area for bone fixation. However, when viewed laterally, as shown in FIG. 1, the lateral side 24L of the lengthwise joist section 24 has a narrow dimension. The narrow dimension provides greater space for receipt of bone graft in the internal open area 50.

In one embodiment, each of the joist structures 20 is preferably about 24 mm in length, from the posterior base 10 to the anterior end 40. The flattened or wide dimension of the support side 24S of the lengthwise joist 24 is preferably between about 1.5 to 3 mm, and preferably 2.5 mm. The narrow dimension of the lateral side 24L of the lengthwise joist 24 is preferably about 1 mm. Thus, in a preferred embodiment, the ratio of the support side 24S to the lateral side 24L is preferably between about 1.5:1 and about 3.0:1, or most preferably about 2.5:1.

The height and width of the cage 1 is preferably about 10 mm. The length of the cage 1 is preferably about 24 mm from the posterior end 10 to the anterior end 40.

To accommodate patient sizes, an assortment of sizes of TLIF cages 1 can be provided. The height of the cages 1 can vary from 7 mm to 14 mm, for example in 1 mm increments. Two or more lengths can be provided, such as 22 mm and 24 mm.

The base frame of the TLIF cage 1 is formed or made of metal to provide strength and rigidity to the cage 1. The metal is preferably a body compatible metal, which will typically be titanium or cobalt chrome. The cage 1 can be used uncoated, in which case the surface is preferably laser sintered to facilitate in-growth of surrounding bone into the surface of the cage. In other embodiments, the cage 1 is preferably over-coated with polyether-ether-ketone (PEEK) 58 circumferentially. The internal rigid first layer of metal, which is typically laser sintered titanium, acts as an internal skeleton, providing strength for the overall device. The PEEK over-coating 58, or second layer, makes the cage 1 partially or completely radiopaque. The second layer 58 functions to increase the surface area superior and inferior for loading against adjacent endplates, and also provides some elasticity to the TLIF structure 1. The superior and inferior loading surfaces 24S may be plasma coated with porous titanium 60 to form a third layer. In other embodiments, the entire PEEK layer is plasma coated with porous titanium. The porous titanium outer coating or layer 60 facilitates bone in-growth for the endplates of the vertebral bodies for improved fixation. The optional PEEK over-coating and titanium plasma coating increase the overall dimensions of the cage 1 by about 17 microns. Alternatively, the metal cage can be downsized so that the aforementioned over-coated embodiments have substantially the same dimensions a sintered titanium embodiment. In yet another embodiment, the cage can be coated with PEEK integrated with hydroxyapatite in lieu of an additional outside layer of titanium.

In the TLIF cage 1 embodiment of FIGS. 1-6, the overall or enveloping volume of the TLIF cage (structure and void) is about 2400 mm$^3$, the volume of the TLIF cage structure (joists and base) is about 583 mm$^3$, and the TLIF void volume 50 is about 1817 mm$^3$. The ratio of the void volume 50 to the enveloping cage volume is preferably between about 0.65 and 0.9, and most preferably about 0.75. The ratio of the void volume 50 to the volume of the TLIF cage structure is preferably between about 2.5 and 4.0, and most preferably about 3.0. These void volume ratios are much higher than the ratios found in conventional TLIF cages, and provide the advantages discussed herein.

A method of manufacturing a composite TLIF device 1 includes first forming or assembling an internal structure or cage 1 from a metal, such as of titanium or cobalt chrome. A coating or layer of PEEK 58 is then applied over all or a substantial portion of the internal cage 1. A coating of porous titanium 60 is then applied to the PEEK 58 second layer and is bonded to the second layer. The porous titanium 60 is applied to the superior and inferior loading surfaces 24S, or optionally to all or a substantial portion of the cage 1. Bone graft can be packed into the internal void volume 50 of the TLIF cage 1. Optionally, a fourth layer, comprising a bioabsorbable condom, can be placed over the TLIF cage to envelop the cage and retain the graft prior to final implantation. The graft packing and enveloping steps can be carried out intra-operatively by the surgeon.

DLIF Cage

Figure 36:
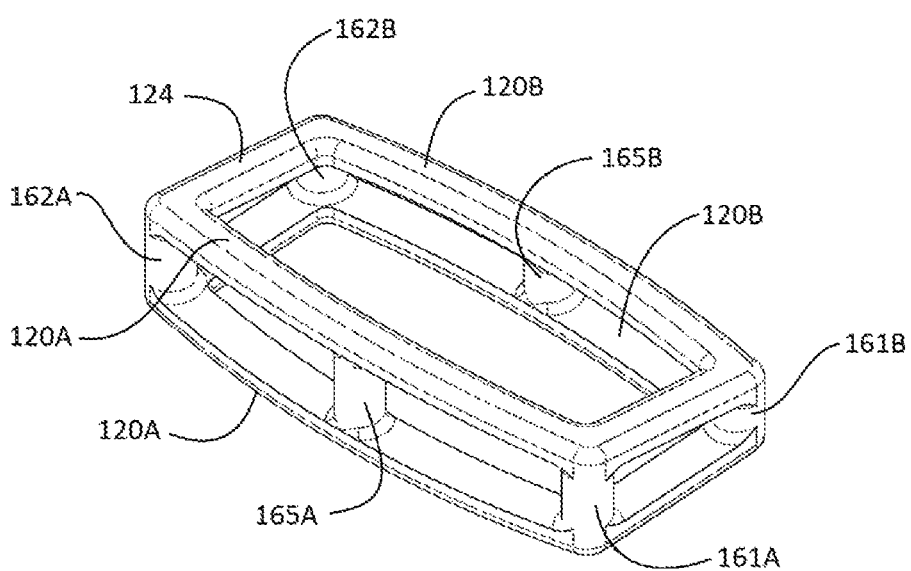
FIG. 36 is a top-front isometric view of one embodiment of a DLIF cage of the invention.
Figure 37:
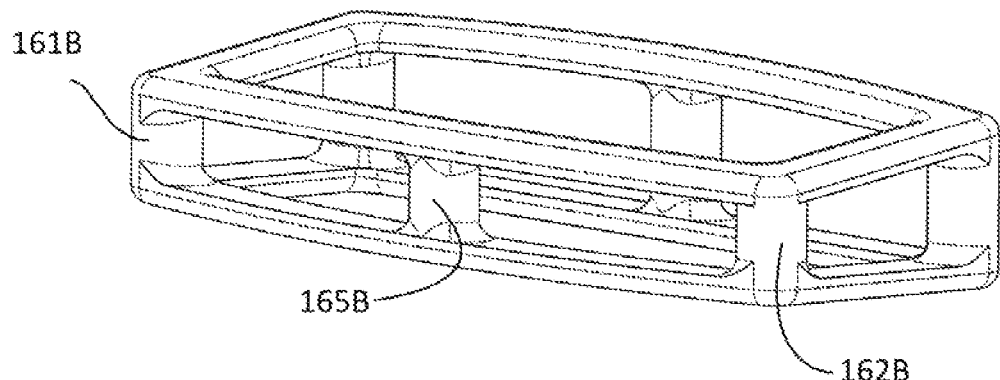
FIG. 37 is a side isometric view of one embodiment of a DLIF cage of the invention.

In an exemplary embodiment of a DLIF cage 100 is shown in FIGS. 35-39. As shown in FIG. 36, the DLIF cage 100 comprises generally a unibody cage portion 102 formed from opposing ring members 170S, 170I and having a voluminous central opening 150. The sides of the DLIF cage 100 have a plurality of large openings 123, 125, 127 formed between support columns 161, 162, 165 and leading into the voluminous void volume 150. Together, the voluminous central opening 150 and side openings 123, 125, 127 contribute to and form a large void volume 103 configured for receipt of bone graft or other adjuncts.

Figure 38:
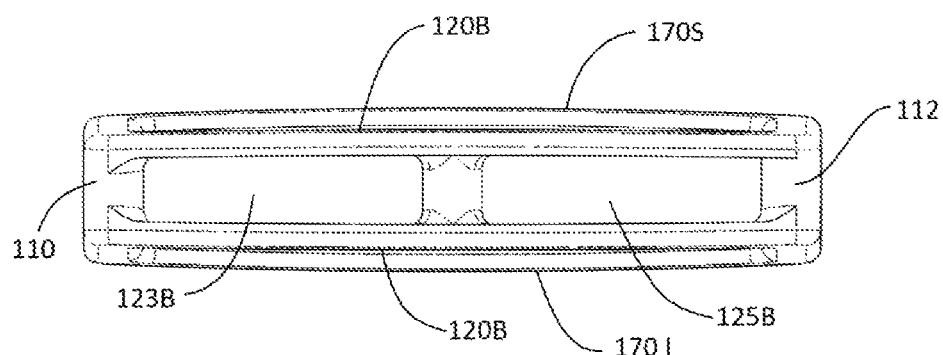
FIG. 38 is a front view of one embodiment of a DLIF cage of the invention.

As indicated in FIG. 38, the DLIF cage portion 102 can be considered to have a superior side surface S and an inferior side surface I. As indicated in FIG. 36, the DLIF cage portion 102 can be considered to have a front or anterior side A and a back or posterior side B. Further, as indicated in FIG. 38, the cage portion 102 can be considered to have a leading or insertion end 112 and a trailing end 110 on lateral sides thereof. A slight slope, for example 1 degree, can be provided between the insertion end 112 and the trailing end 110.

Figure 39:
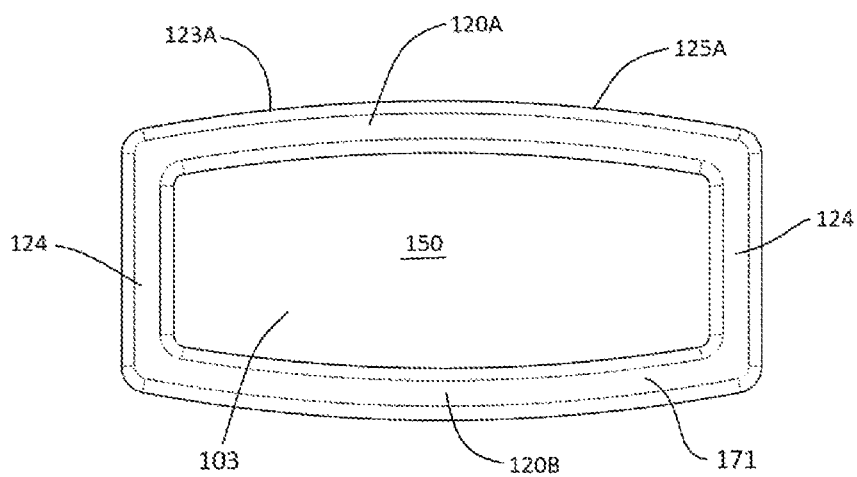
FIG. 39 is a top view of one embodiment of a DLIF cage of the invention.

As indicated in FIG. 36, a first or superior side of the cage 102 is formed from a generally planar ring member 170S, while a second or inferior side of the cage 102 is formed from an opposing generally planar ring member 170I. The opposing ring members 170S, 170I are maintained in spaced relationship by a plurality of strut members 161, 162, 165. The strut members 161, 162, 165 may be integrally formed with the ring members 170S, 170I. Each ring member 170S, 170I is formed from a first or anterior lengthwise joist 120A and a second or posterior lengthwise joist 120B. The anterior and posterior joists 120A, 120B are interconnected by a pair of opposing lateral joists 124, the joists 120A, 120B, 124 together forming an integral surface 171. As shown in FIG. 39, the various joists 120A, 120B, 124 are preferably joined at their respective ends. In the embodiment of FIGS. 35-39, the inferior side ring member 170I of the cage portion 102 presents substantially a mirror image of the superior ring member 170S.

As shown in FIG. 39, the superior and inferior ring members 170S, 170I are interconnected by a plurality of struts 161, 162, 165. In the embodiment shown, a pair of anterior struts 161A, 162A interconnect opposing ends of the anterior superior and inferior joists 120. Likewise, a pair of posterior struts 162A, 162B interconnect opposing ends of the posterior superior and inferior joists 322S, 322I. A central pair of struts 165A, 165B is provided for distributing vertical load. For maximum strength, the struts 161, 162, 165 are sandwiched between and integrally formed with the superior and interior sides 170S, 170I.

In the embodiment of FIG. 39, each of the first and second lengthwise joist portions 120A, 120B is bowed outward, such that each lengthwise joist 120A, 120B is arcuate. As indicated in FIG. 39, this arrangement enables a large central cavity or void volume 150 within the cage portion 102. Each of the lengthwise joist portions 120 may be centrally bowed away from the centerline of the cage 100 and peaked at the center strut 165A, 165B so as to strengthen the joists, provide additional strength, and increase the open area.

The sides formed by the spaced lengthwise joist portions 120A, 120B and cross joists 124 preferably have at least one side opening 123 passing therethrough. As seen in the anterior/posterior side view of FIG. 38, each of the joists 120 preferably has a first or lateral side opening 123 and a second or medial side opening 125. As indicated in FIG. 38, each side opening 123, 125 passes entirely through a sidewall of the joist 120, such that the void volume 150 communicates with the exterior through the openings 123, 125. This configuration facilitates release of bone graft from the void volume 150 into the vertebral space adjacent the cage 100. The side openings 123, 125 are sized and configured such that the strength of the joist portions 120 and cage structure 102 not significantly compromised while maximizing the potential for release of graft through the openings 123, 125.

Preferred dimensions of the DLIF cage of FIGS. 35-39 will now be described. It is expected that due to various anatomical sizes in the patient population, various sizes of DLIF cages 100 according to the invention will be provided, such as in an implant kit or surgical tray. Thus, variations from these dimensions may be made without deviating from the spirit and scope of the invention. The length of the cage portion 102, measured from the first lateral side 110 to the second lateral side 112, is preferably 50 mm. The width of the cage portion 102, measured from the outer edge of the peaks of the first and second opposing lengthwise joists 120A, 120B is preferably 25 mm. The height of the cage portion 102, is preferably between about 9 to 10 mm. In sloped embodiments, the cage portion may have a slope of about 8 degrees. The height of the cage portion 102 on the leading side may be about 9 mm (e.g. 9.1 mm), while the height on the trailing side may be about 10 mm. The joists 120, 124 are preferably about 4 mm wide and about 2 mm thick. The support struts 161, 162, 165 may have a major diameter of about 4 mm.

To accommodate patient sizes, an assortment of sizes of DLIF cages 100 can be provided. The height of the cages 100 can vary from about 8 mm to 16 mm, for example in 1 mm increments. Two, three or more lengths can be provided, such as 48, 50 and 52 mm. Two, three or more widths can also be provided, such as 23, 24 and 25 mm. Various lordosis angles can be provided, such as 8 degrees.

In a preferred embodiment, the enveloping volume of the DLIF cage is between about 11,500 $mm^3$ to about 13,500 $mm^3$, such as about 12,500 $mm^3$. The net enveloping volume is between about 11,000 $mm^3$ to 13,000 $mm^3$, such as about 11,938 $mm^3$.

The material volume of the DLIF cage structure is between about 1800 $mm^3$ to about 2000 $mm^3$, such as about 1868 $mm^3$. The void volume is between about 9,500 $mm^3$ to about 11,500 $mm^3$, such as about 10,632 $mm^3$. The net void volume is between about 9,000 $mm^3$ to about 11,000 $mm^3$, such as about 10,069 $mm^3$.

The ratio of the void volume to the enveloping volume is preferably between about 0.75 to about 0.9, such as about 0.85. The ratio of the net void volume to the net enveloping volume is preferably about 0.75 to about 0.9, such as about 0.84.

The ratio of the void volume to the material volume of the DLIF cage structure is preferably between about 5.0 to about 6.5, such as about 5.69. The ratio of the net void volume to the material volume is between about 4.8 to about 6.3, such as about 5.39. These void volume ratios are much higher than the ratios found in conventional DLIF cages, and provide the advantages discussed herein.

DLIF Cage with Rotational Plate

FIGS. 7-13 show views of one embodiment of applicant's DLIF cage having a rotational plate 100. As shown in the perspective view of FIG. 7, the DLIF cage 100 comprises generally a unibody cage portion 102 having a voluminous central opening or void volume 150 configured for receipt of bone graft or other adjuncts and a rotational plate 180 rotatably disposed on a first lateral side 110 of the cage portion 102.

Figure 8:
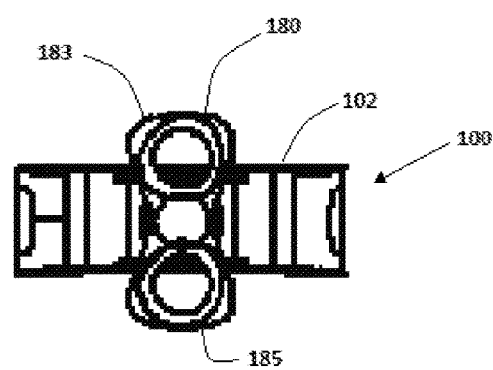
FIG. 8 is a rear view of one embodiment of a DLIF cage of the invention showing a rotational plate in an insertion orientation.

As shown in FIG. 8, the rotational plate 180 is provided with first and second opposing screw bores 183, 185 configured for receipt of spinal bone screws. The screw bores 183, 185 will typically be unthreaded, so as to allow the surgeon to select the screw insertion angle, which allows for polyaxial fixation.

Figure 9:
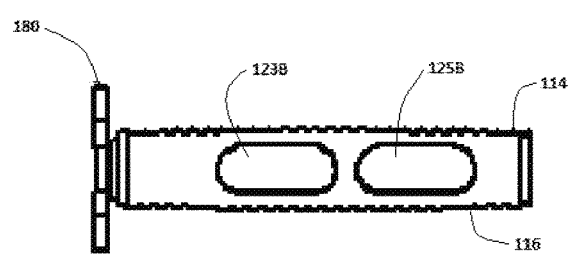
FIG. 9 is a side view of one embodiment of a DLIF cage of the invention showing a rotational plate in an attachment orientation.
Figure 10:
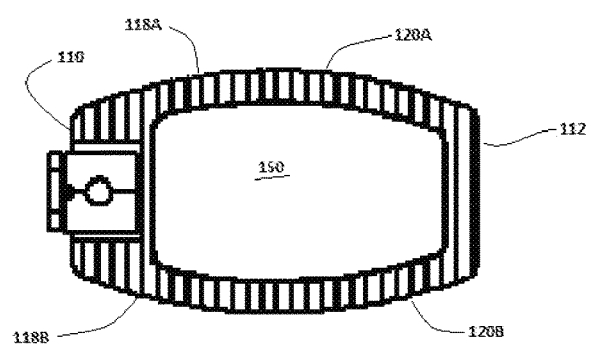
FIG. 10 is a top view of one embodiment of a DLIF cage of the invention showing a rotation plate in an attachment orientation.
Figure 11:
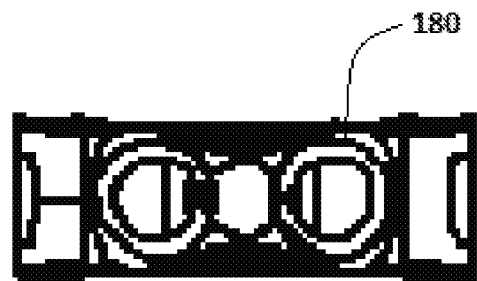
FIG. 11 is a rear view of one embodiment of a DLIF cage of the invention showing a rotational plate in an insertion orientation.
Figure 12:
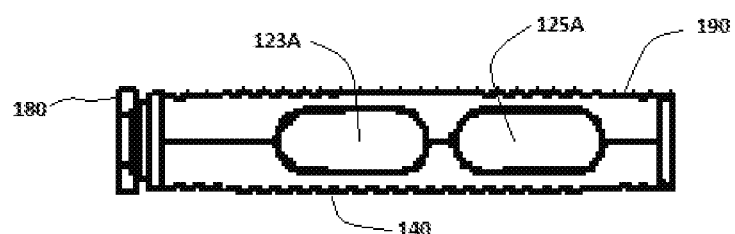
FIG. 12 is a side view of one embodiment of a DLIF cage of the invention showing a rotational plate in an insertion orientation.
Figure 13:
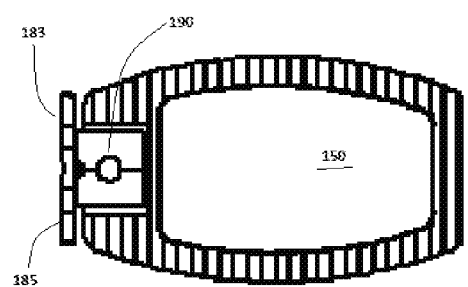
FIG. 13 is a top view of one embodiment of a DLIF cage of the invention showing a rotational plate in an insertion orientation.

FIGS. 11-13 show the rotational plate 180 in an insertion configuration in which the plate portion 180 is rotated to or aligned with the first lateral side 110 at about zero degrees, in a horizontal plane orientation. In contrast, FIGS. 7-10 show the rotational plate 180 in a fixation configuration in which the plate 180 has been rotated 90 degrees, into a vertical plane orientation. In this configuration, the surgeon can selectively secure the DLIF cage 100 to the lumbar vertebrae by passing screws through one or both of the first and second screw bores 183, 185. In addition to the zero and 90 degree positions shown in the drawings, the surgeon has the option of rotating the plate to any desired position relative to the patient's internal anatomy. Thus, the DLIF cage with rotational plate 100 is configured for insert into the lumbar space and to allow for selection of and fixation to a preferred location of anatomical bone. This selective capability is particularly useful when operating on patients who have soft or otherwise compromised bone, where it may be difficult or impossible to adequately secure a plate in certain regions of the lumbar vertebrae.

As can be seen in FIG. 10, the cage portion 102 includes a first lateral side 110, a second or opposing lateral side 112, and first and second lengthwise strut portions 120A, 120B extending between the first and second lateral sides 110, 112. In the embodiment of FIG. 10, each of the first and second lengthwise strut portions 120A, 120B is bowed outward, such that each lengthwise strut 120A, 120B is arcuate. As indicated in FIG. 10, this arrangement enables a large central cavity or void volume 150 within the cage portion 102.

At least one of the lengthwise strut portions 120 preferably has at least one side opening 123 passing therethrough. As seen in the anterior/posterior side view of FIG. 9, each of the struts 120 preferably has a first or lateral side opening 123 and a second or medial side opening 125. As indicated in FIGS. 9 and 12, each side opening 123, 125 passes entirely through a sidewall of the strut 120, such that the void volume 150 communicates with the exterior through the openings 123, 125. This configuration facilitates release of bone graft from the void volume 150 into the vertebral space adjacent the cage 100. The side openings 123, 125 are sized and configured such that the strength of the strut portions 120 and cage structure 102 not significantly compromised while maximizing the potential for release of graft through the openings 123, 125.

As can be seen in the embodiment of FIG. 12, a plurality of loading surface designs 140 are provided or formed on both the superior 114 and inferior 116 sides of the cage portion 102. In the embodiment shown in the drawings, the loading surface designs 140 are ridges 140 arranged in parallel rows aligned along the anterior-posterior dimension of the cage 102. However, other configurations could be used for the loading surface designs 140, such as crosshatches, broken rows, or medial-lateral rows. Alternatively, the bone engagement surface of the DLIF cage 100 can be smooth (not shown). In all surface embodiments, porous titanium can be used for bone ingrowth.

The DLIF cage portion 102 is preferably formed of PEEK material, but it can be made of other biocompatible metals, such as titanium or cobalt chrome.

In an alternative embodiment, the rotational plate 180 is provided on a separate clip (not shown). The separate clip is preferably made of PEEK and the rotational plate is made of metal. The separate clip is configured to clip onto lateral struts, such as a pair of lateral struts, formed on the DLIF cage 100. Alternatively, the separate clip and the rotational plate can be made of PEEK, or both can be made of metal.

A shaving instrument (not shown) can be provided for preparing the lateral aspect of the vertebral body to allow the plate to rotate freely relative to the vertebrae prior to screw placement. The instrument will progressively clear a space, such as an annular space, in the bone adjacent the implant site to allow the plate to rotate freely until a final position for the plate is selected.

ALIF Cage with Side Clip

Figure 14:
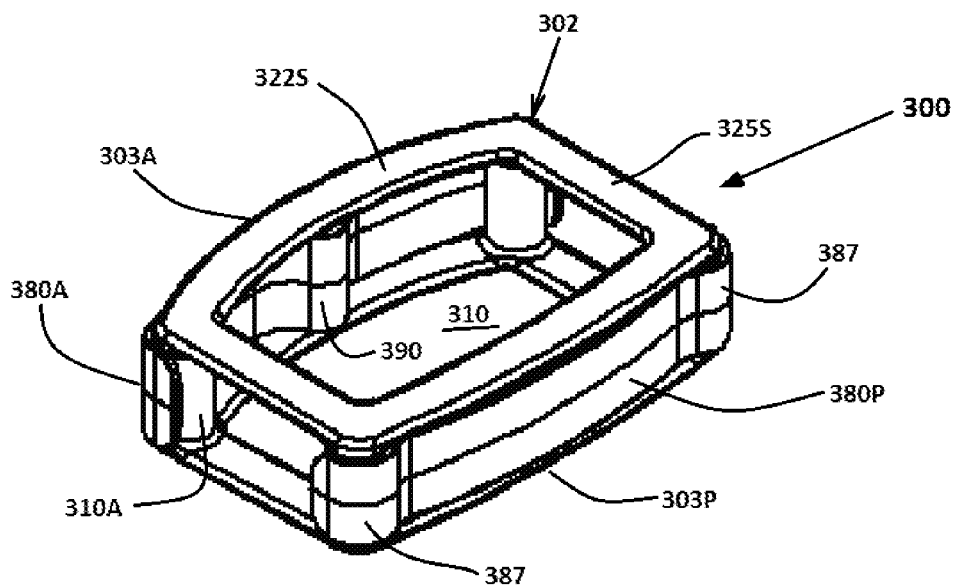
FIG. 14 is a rear-side isometric view of one embodiment of an ALIF cage of the invention.
Figure 15:
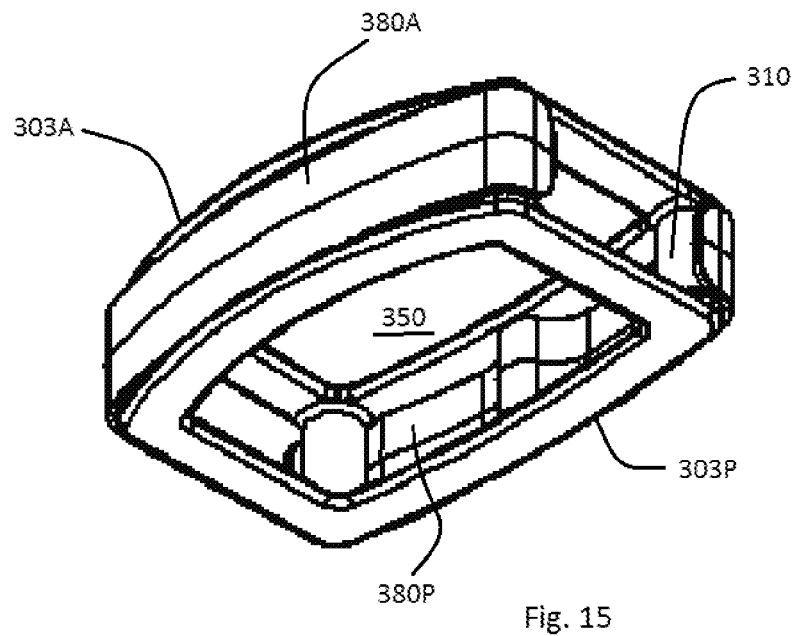
FIG. 15 is a front-side isometric view of one embodiment of an ALIF cage of the invention.
Figure 16:
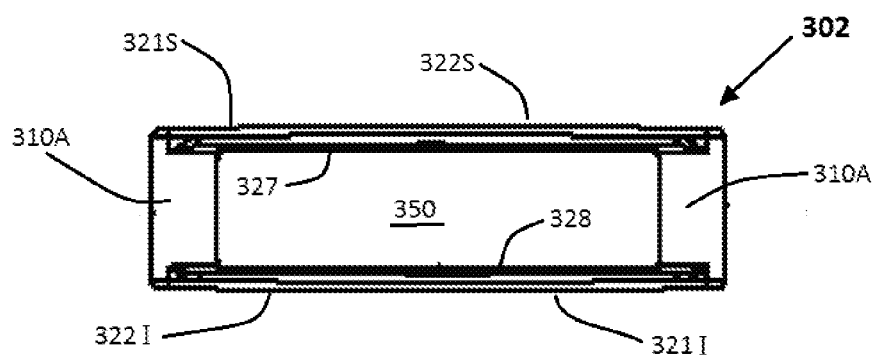
FIG. 16 is a front view of one embodiment of an ALIF cage of the invention.
Figure 17:
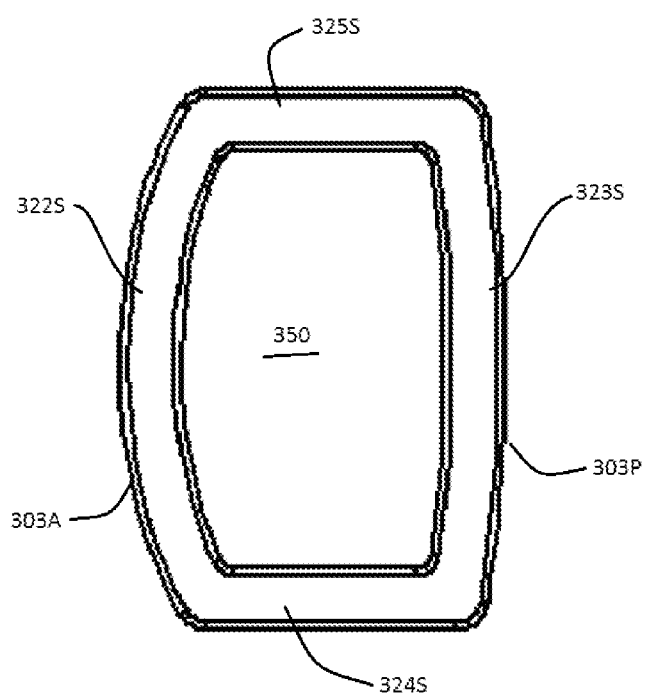
FIG. 17 is a top view of one embodiment of an ALIF cage of the invention.
Figure 18:
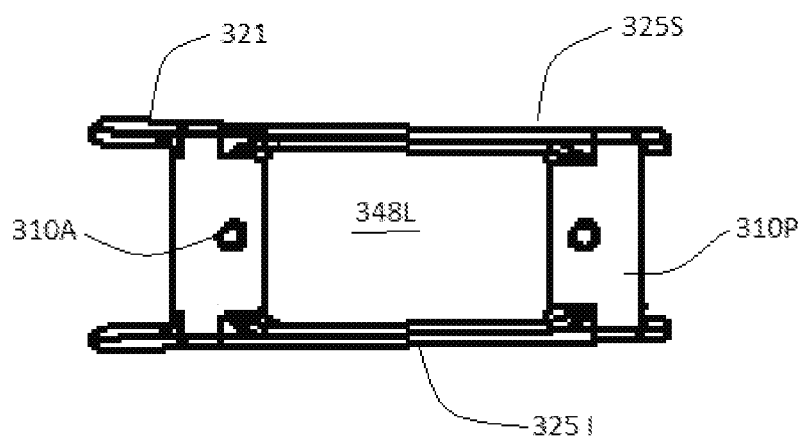
FIG. 18 is a side view of one embodiment of an ALIF cage of the invention.
Figure 19:
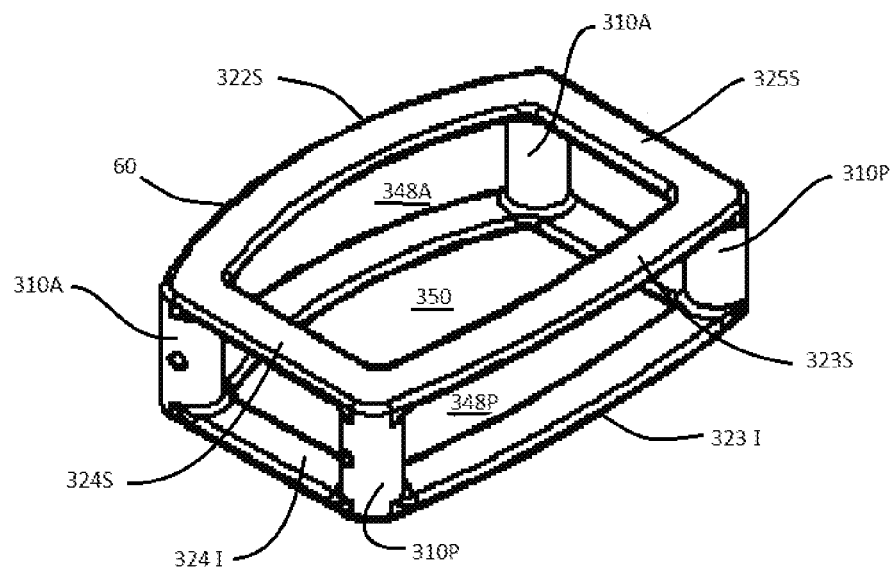
FIG. 19 is a rear-side isometric view of one embodiment of an ALIF cage of the invention.
Figure 20:
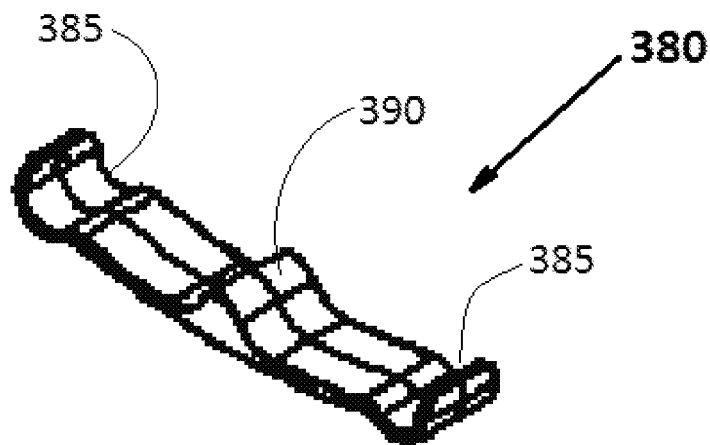
FIG. 20 is an isometric view of one embodiment of a clip for an ALIF cage of the invention.

FIGS. 14-23 show views of embodiments of applicant's ALIF cage 300. As shown in the perspective view of FIG. 14, the ALIF cage of the invention 300 generally comprises a cage portion 302 having a voluminous interior cavity or void volume 350, large side openings 348A, 348P, 348L, and snap-on/clip-on anterior and posterior side caps 380A, 380P for use in selectively sealing the anterior and posterior side openings 348A, 348P. The cage portion 302 is formed from opposing superior and inferior joist portions 322, 323, 324, 325 which are interconnected and spaced apart by a plurality of support struts 310, as will be described below. As indicated in FIG. 16, the cage portion 302 has a superior side surface 321S and an inferior side surface 321I. As indicated in FIG. 17, the cage portion has an anterior side 303A and a posterior side 303P. As shown in the top or superior view of FIG. 17, the superior side surface 321S is formed from a superior anterior joist 322S and an opposing superior posterior joist 323S. The superior anterior and posterior joists 322S, 323S are interconnected by a pair of opposing superior lateral joists 324S, 325S, the joists together forming an integral superior surface 321S. As shown in FIG. 17, the various jousts 322S, 323S, 324S, 225S are preferably joined at their respective ends. The inferior side surface 321I of the cage portion 302 preferably presents substantially a mirror image of the superior side 321S, with an inferior anterior joist 322I and an inferior posterior joists 323I interconnected by a pair of inferior lateral joists 324I, 325I. As shown in FIG. 19, the superior and inferior sides 321S, 321I are interconnected by a plurality of struts 310. In the embodiment shown, a pair of anterior struts 310A interconnect opposing ends of the anterior superior and inferior joists 321S, 321I. Likewise, a pair of posterior struts 310P interconnect opposing ends of the posterior superior and inferior joists 322S, 322I. For maximum strength, the struts 310A, 310P are sandwiched between and integrally formed with the superior and interior sides 321S, 321I.

The ALIF cage portion 302 includes various features that facilitate an ALIF procedure. As can be seen in the top view of FIG. 17, the anterior joist 322 is bowed outwards anteriorly in an arcuate manner. The posterior joist 323 is bowed outwards posteriorly, but in a more flattened or gentle curve than the anterior joist 323. The lateral joists 324, 325 are preferably straight. As indicated in FIG. 18, an anterior-to-posterior lordosis slope is preferably built into the cage portion 302. The lordosis slope is preferably about 6-10 degrees, and most preferably about 8 degrees. Larger slopes can be used to provide greater lordosis. The slope can be built into both sides of the cage 302, in which case the slope will be about 4 degrees per side, or built into only one side of the cage 302, such that one side is flat and the other side has a slope of about 8 degrees. This slope can be facilitated by making the anterior struts 310A longer than the posterior struts 310P. In one preferred embodiment, the anterior struts 310A are 9 mm in height while the posterior struts 310P are 8 mm in height.

The described cage structure 302 provides a relatively large void volume 350 relative to the volume of the cage structure 302, as well as large superior and inferior openings and large anterior, posterior and opposing side openings 348A, 348P, 348L. This allows for the use of a large amount of bone graft in the void volume 350, as well as release of the graft through the openings. Use of the void volume 350 and openings is further facilitated by selective use of the ALIF clips 380, as described below. However, despite the large void volume 350 and openings, the structure of the cage 302, as described herein, provides the cage 302 with sufficient strength for use as an ALIF implant.

The ALIF cage portion 302 is formed from a bio-compatible metal such as titanium or cobalt chrome. At least a portion of the outer surface of the ALIF cage portion 302 is laser-sintered with a plasma titanium powder coating 60 for optimal bony in-growth and secure fixation against vertebral endplates. In one embodiment, the entire surface of each of the loading superior and inferior outer surfaces 321S, 321I are plasma coated with titanium 60.

Details of embodiments of the anterior and posterior side caps 380A, 380P will now be discussed. As shown in FIGS. 14-15, the anterior and posterior side caps 380A, 380P are configured to snap-on to the struts 310 of the cage 302. In an embodiment shown in FIGS. 20-23, each side cap 380 comprises a unibody structure including a pair of wings 391, 392.

Figure 22:
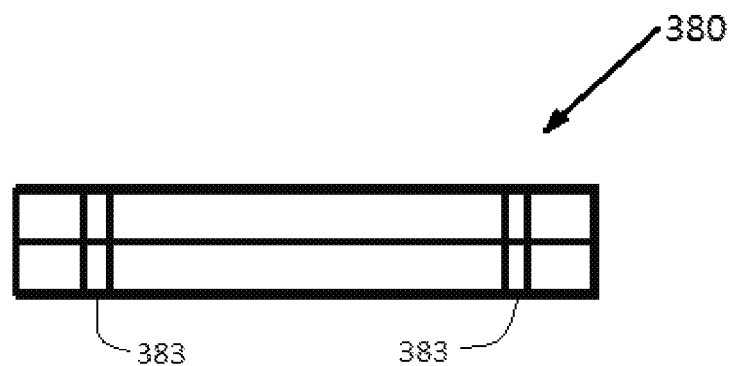
FIG. 22 is an outside view of one embodiment of a clip for an ALIF cage of the invention.
Figure 23:
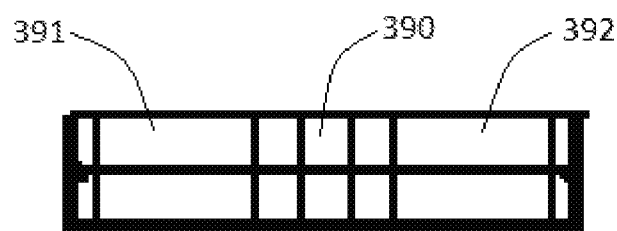
FIG. 23 is an inside view of one embodiment of a clip for an ALIF cage of the invention.

Opposing ends of each wing 391, 392 are provided with an annular wall 387 formed on the inner surface 381 of the ALIF cap 380. When viewed from an exterior or outer side 382, a bend 383 is formed in the juncture where the annular wall 387 begins, as shown in FIG. 22. Each annular wall 387 encloses a respective inner cavity 386. A portion of the annular wall 387 extends beyond 180 degrees, leaving an opening for receipt of a strut 310 of the ALIF cage 302 into the cavity 386, in a snap-fit engagement. By "snap-fit engagement," it will be understood that annular wall 387 is sufficiently resilient to deflect or compress elastically so as to store elastic energy when a strut 310 is pushed into cavity 386. The annular wall 387 has an inner diameter that is complementary to an outer diameter of the strut 310, but slightly larger in size, so as to secure the cap 380 on the struts 310 while minimizing motion between the cap 380 and the ALIF cage 302.

Figure 21:
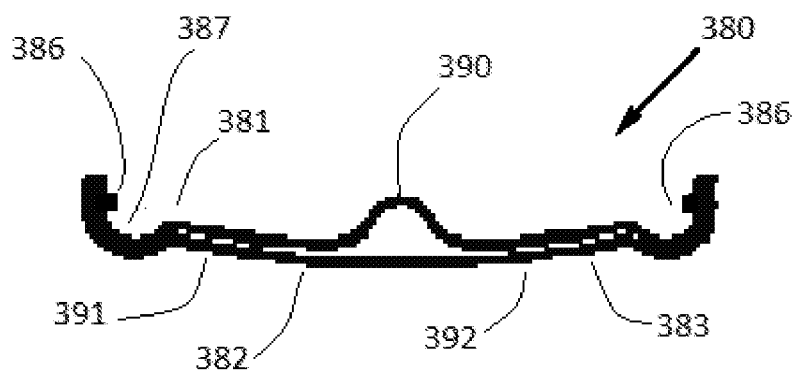
FIG. 21 is a top view of one embodiment of a clip for an ALIF cage of the invention.

To further enhance the ALIF cage construct 300, one or both of the caps 380 is preferably provided with an inner strut 390, as shown in FIGS. 20-23. The inner strut 390 is sized and configured to provide additional loading support between the inferior and superior joists 319, 320 when attached to the ALIF cage 302. As shown in FIG. 21, the inner strut 390 is preferably formed on the inner surface 381 of the cap 380, and is preferably centered or substantially centered on the cap 380, between the opposing wings 391, 392. The inner strut 390 preferably has a rounded peak and a rounded or sloped interface with the inner surface 381 of the cap 380. As can be appreciated from the construct views of FIGS. 14-15, when the cap 380 is attached to the cage 302, the height of the inner strut 390 is dimensioned so as to abut against the inferior surface 327 of the superior joists 322S, 323S and the superior surface 328 of the inferior joists 322I, 323S. In this manner, the inner struts 390 provide load support between the joists 322, 323, and particularly between the central portions of the joists, where compressive forces from the vertebrae receive less countervailing support from the cage struts 310. Thus, the large openings 348A, 348P on the anterior and posterior sides of the cage 302 facilitate the use of interbody graft, while the removable caps 380 selectively enclose the openings 348A, 348P while providing supplemental loading support akin to that provided by the cage struts 310.

The posterior and anterior side caps 380A, 380P are preferably made of PEEK. Other materials can be used, provided that such materials are biocompatible and enable the side caps 380A, 380P to selectively snap on to or off of the struts 310 in a sufficiently secure engagement.

Preferred dimensions of the ALIF cage 302 and clips 380 will now be described. It is expected that due to variations in anatomical size in the patient population, various sizes of ALIF cage constructs 300 according to the invention will be provided, such as in an implant kit or surgical tray. Thus, it will be appreciated that variations from these dimensions may be made without deviating from the spirit and scope of the invention.

In one preferred embodiment, the ALIF cage 302 of the invention has a length of 37 mm, a depth of 27 mm, and a maximum height of 10 mm. The joists 322, 323, 324, 325 have a height of only 1.5 mm when viewed from the posterior or anterior side, as indicated in FIG. 16. The joists 322, 323, 324, 325 have a width of 4 mm when viewed from the top or bottom, as indicated in FIG. 17.

The struts 310 have a diameter of 4 mm. The anterior struts 310 have a height of 10 mm, while the posterior struts 310 have a height of 9 mm. This provides the aforementioned anterior-to-posterior slope of about 8 degrees.

The ALIF clip 380 has a length of 37 mm, or approximately the length of the ALIF cage 302. The center strut 390 has a depth or height of 4.5 mm. The wings 391, 392 have a depth or height of 4.5 mm and are 0.75 mm thick. The height of the anterior ALIF clip 380 is 7 mm, in order to substantially fill the anterior opening 348A. Likewise, the height of the posterior ALIF clip 380 is 6 mm, which substantially fills the posterior opening 348P.

To accommodate patient sizes, an assortment of sizes of ALIF cages 300 can be provided. The height of the cages 300 can vary from about 8 mm to 16 mm, for example in 1 mm increments. Two, three or more lengths can be provided, such as 35, 37 and 39 mm. Two, three or more widths or depths can also be provided, such as 26, 27 and 28 mm. Various lordosis angles can be provided.

In a preferred embodiment, the overall volume of the ALIF cage (structure and void) is about 9900 $mm^3$, the volume of the ALIF cage structure (joists and struts) is about 1821 $mm^3$, and the ALIF void volume 350 is about 8,169 $mm^3$. The ratio of the void volume 350 to the overall cage volume is preferably between about 0.7 and 0.9, and most preferably about 0.8. The ratio of the void volume 350 to the volume of the ALIF cage structure is preferably between about 4.2 and 4.7, and most preferably about 4.5. These void volume ratios are much higher than the ratios found in conventional ALIF cages, and provide the advantages discussed herein.

In one exemplary embodiment, the ALIF cage structure has a width of about 25 mm, a length of about 35 mm, a minimum height of 6.5 mm, a maximum height of 9.8 mm, and a lordosis angle of 8 degrees. The joists have a width of 4 mm and a thickness of 1.5 mm.

In an exemplary embodiment, the enveloping volume of the ALIF cage is between about 7,500 $mm^3$ to about 9,500 $mm^3$, such as about 8,575 $mm^3$. The net enveloping volume is between about 6,000 $mm^3$ to about 8,000 $mm^3$, such as about 7,131 $mm^3$.

The material volume of the ALIF cage structure is between about 1,100 $mm^3$ to about 1,700 $mm^3$, such as about 1,398 $mm^3$. The void volume is between about 6,000 $mm^3$ to about 8,000 $mm^3$, such as about 7176 $mm^3$. The net void volume is between about 4500 $mm^3$ to about 7,000 $mm^3$, such as about 5732 $mm^3$.

The ratio of the void volume to the enveloping volume is preferably between about 0.7 to about 0.9, such as about 0.84. The ratio of the net void volume to the net enveloping volume is preferably about 0.7 to about 0.9, such as about 0.80.

The ratio of the void volume to the material volume of the ALIF cage structure is preferably between about 4.6 to about 5.6, such as about 5.13. The ratio of the net void volume to the material volume is between about 3.6 to about 4.6, such as about 4.1. These void volume ratios are much higher than the ratios found in conventional ALIF cages, and provide the advantages discussed herein.

An important objective of the implants of the invention is to provide a greater volume of bone graft as well as optimized communication with the surrounding disk space area. The cages allow for a high volumetric expansion of bone graft. For example, the TLIF cage of the invention allows for the use of about 6-8 times more bone graft than a conventional TLIF cage, such as TLIF cages commercially available from Medtronic. The cages of the invention also allow the graft material to fully communicate with the disk space while maintaining support of the disc space.

For each of the cages of the invention, the minimal frame structures allow, in addition to the use of greater amounts of graft material, a minimal radiographic foot print compared to conventional LIF or ACDF cages. This characteristic allows for greater visualization when viewing and monitoring the post-operative progression of interbody fusion.

For each of the cages of the invention, the titanium surface is preferably configured to allow for bone in-growth on some or all of the outer surfaces of the cage. Sintering can be used to achieve an appropriate in-growth surface, in a manner known in the art. Alternatively, in some embodiments, the cage can be coated with PEEK integrated with hydroxyapatite in lieu of an additional outside layer of titanium.

When PEEK is applied to one of the frames described herein, it can be applied in various ways. One method is to spray PEEK onto the metal frame of the cage. The sprayed PEEK is preferably implant grade PEEK. Although spraying of industrial grade PEEK to form a coating has been used outside of the medical implant field, applicants are unaware of the previous use of spraying of implantable PEEK onto implants. Another method is to dip or submerge the cage into a solution of PEEK and then remove the cage from the PEEK solution. Brushing or other methods can be used, provided that the PEEK sufficiently covers and adheres to the underlying frame.

One of the advantages of the invention is that it works with commercially available bone graft materials while enhancing the ability of such bone grafts to fuse vertebrae. Bone grafts promote bone healing through an osteogenic, osteoconductive or osteoinductive mechanism. Examples of grafts that could be used with the cages of the invention include autografts and allografts. The graft can include natural or recombinant BMPs or bone marrow aspirate. The graft can be in the form of putties, pastes or granules, or combinations thereof, and can include antibiotic or other anti-bacterial agents. A commercial brand that could be used with the cages of the invention is INFUSE® bone graft from Medtronic.

Anterior Cervical Discectomy Fusion Cage

FIGS. 24-28 show views of embodiments of applicant's anterior cervical discectomy fusion (ACDF) cage 1300. The ACDF cage 1300 incorporates features of the ALIF cage as well as the general characteristics and advantages described herein with respect to lumbar interbody fusion cages.

Figure 24:
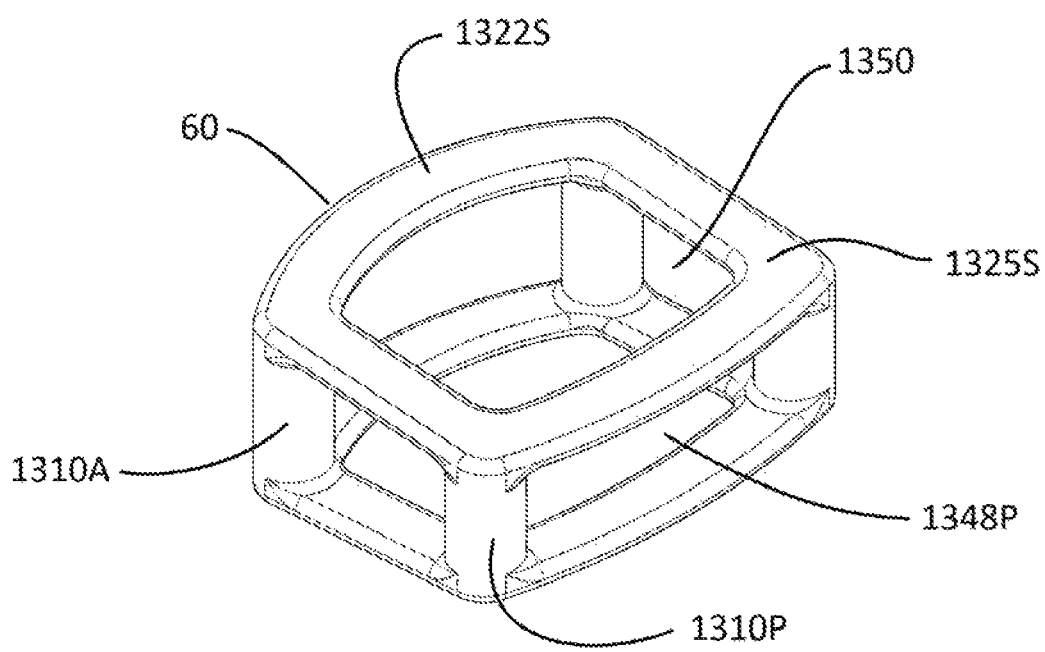
FIG. 24 is a rear-side isometric view of one embodiment of an anterior cervical discectomy fusion cage of the invention.
Figure 25:
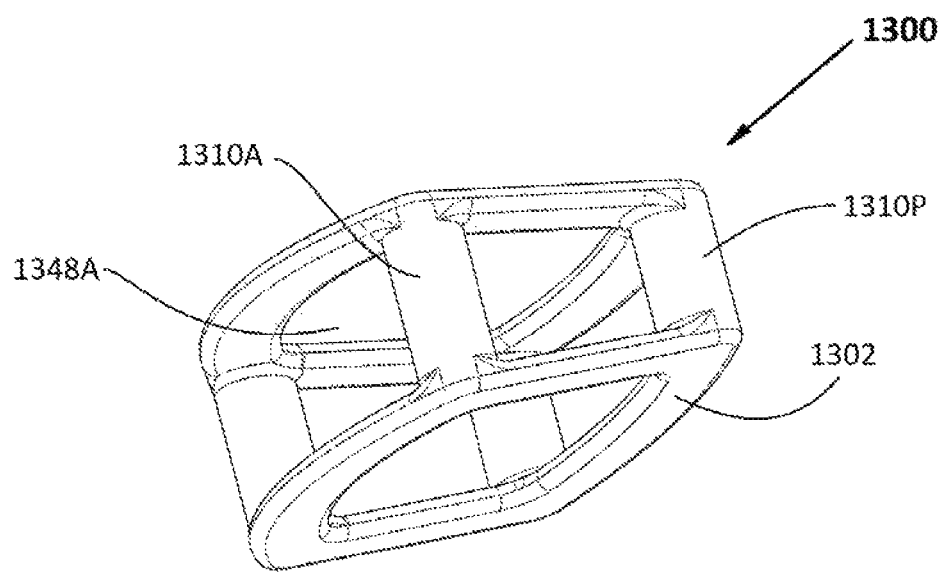
FIG. 25 is a front-side isometric view of one embodiment of an anterior cervical discectomy fusion cage of the invention.

As shown in the perspective view of FIG. 24, the ALIF cage of the invention 300 generally comprises a cage portion 1302 having a voluminous interior cavity or void volume 1350, and large side openings 1348A, 1348P, 1348L. The cage portion 1302 is formed from opposing superior and inferior joist portions 1322, 1323, 1324, 1325 which are interconnected and spaced apart by a plurality of support struts 1310, as will be described below.

Figure 26:
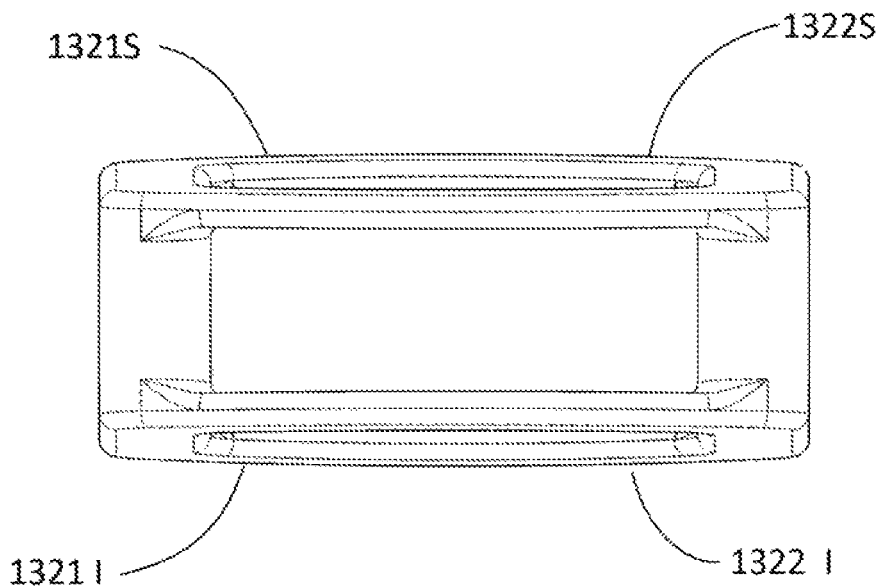
FIG. 26 is a front view of one embodiment of an anterior cervical discectomy fusion cage of the invention.
Figure 27:
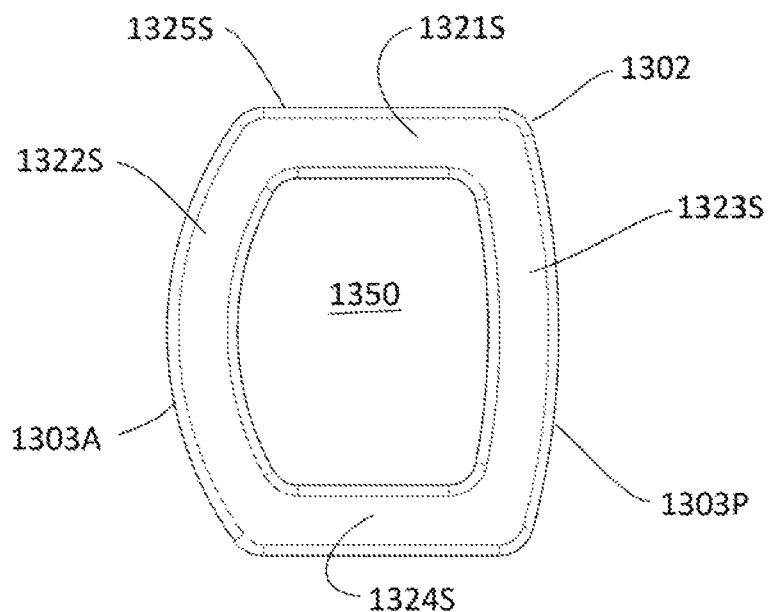
FIG. 27 is a top view of one embodiment of an anterior cervical discectomy fusion cage of the invention.

As indicated in FIG. 26, the cage portion 1302 has a superior side surface 1321S and an inferior side surface 1321I. As indicated in FIG. 27, the cage portion 1302 has an anterior side 1303A and a posterior side 1303P. As shown in the top or superior view of FIG. 27, the superior side surface 1321S is formed from a superior anterior joist 1322S and an opposing superior posterior joist 1323S. The superior anterior and posterior joists 1322S, 1323S are interconnected by a pair of opposing superior lateral joists 1324S, 1325S, the joists together forming an integral superior surface 1321S. As shown in FIG. 27, the various jousts 1322S, 1323S, 1324S, 1225S are preferably joined at their respective ends. The inferior side surface 1321I of the cage portion 1302 preferably presents substantially a mirror image of the superior side 1321S, with an inferior anterior joist 1322I and an inferior posterior joist 1323I interconnected by a pair of inferior lateral joists 1324I, 1325I. As shown in FIG. 24, the superior and inferior sides 1321S, 1321I are interconnected by a plurality of struts 1310. In the embodiment shown, a pair of anterior struts 1310A interconnect opposing ends of the anterior superior and inferior joists 1321S, 1321I. Likewise, a pair of posterior struts 1310P interconnect opposing ends of the posterior superior and inferior joists 1322S, 1322I. For maximum strength, the struts 1310A, 1310P are sandwiched between and integrally formed with the superior and interior sides 1321S, 1321I.

Figure 28:
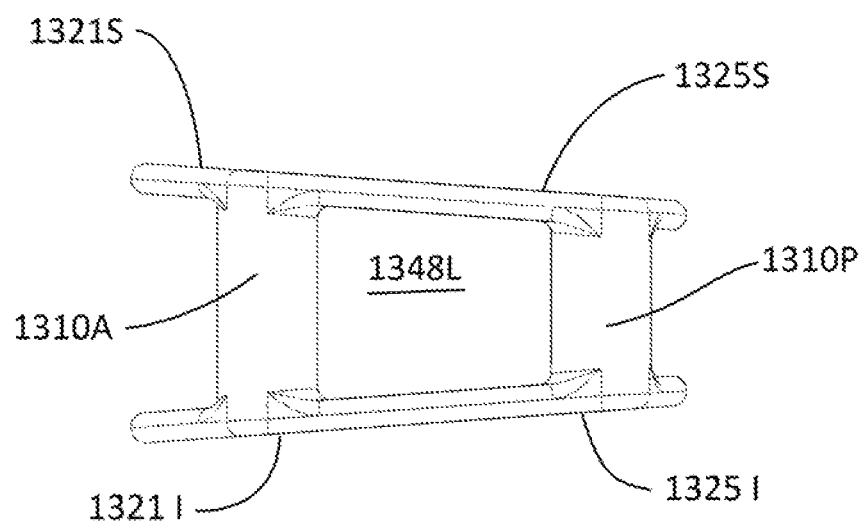
FIG. 28 is a side view of one embodiment of an anterior cervical discectomy fusion cage of the invention.

The ACDF cage portion 1302 includes various features that facilitate a ACDF procedure. As can be seen in the top view of FIG. 27, the anterior joist 1322 is bowed outwards anteriorly in an arcuate manner. The posterior joist 1323 is bowed outwards posteriorly in an arcuate manner. The lateral joists 1324, 1325 are preferably straight. As indicated in FIG. 28, an anterior-to-posterior slope is preferably built into the cage portion 1302. The slope is preferably about 7 to 9 degrees, and most preferably about 8 degrees. The slope can be built into both sides of the cage 1302, in which case the slope will be about 4 degrees per side, or built into only one side of the cage 1302, such that one side is flat and the other side has a slope of about 8 degrees. This slope can be facilitated by making the anterior struts 1310A longer than the posterior struts 1310P. In one embodiment, the anterior struts 1310A are about 4.8 mm in height while the posterior struts 1310P are about 3.9 mm in height.

The described cage structure 1302 provides a relatively large void volume 1350 relative to the volume of the cage structure 1302, as well as large superior and inferior openings and large anterior, posterior and opposing side openings 1348A, 1348P, 1348L. This allows for the use of a large amount of bone graft in the void volume 1350, as well as release of the graft through the openings. However, despite the large void volume 1350 and openings, the structure of the cage 1302, as described herein, provides the cage 1302 with sufficient strength for use as a ACDF implant.

The ACDF cage portion 1302 is formed from a biocompatible metal such as titanium or cobalt chrome. At least a portion of the outer surface of the ACDF cage portion 1302 is laser-sintered with a plasma titanium powder coating 60 for optimal bony in-growth and secure fixation against vertebral endplates. In one embodiment, the entire surface of each of the loading superior and inferior outer surfaces 1321S, 1321I are plasma coated with titanium 60.

Preferred dimensions of the ACDF cage 1302 will now be described. It is expected that due to variations in anatomical size in the patient population, various sizes of ACDF cage constructs 1300 according to the invention will be provided, such as in an implant kit or surgical tray. Thus, it will be appreciated that variations from these dimensions may be made without deviating from the spirit and scope of the invention.

To accommodate patient sizes, an assortment of sizes of ACDF cages 1300 can be provided. The height of the ACDF cages 1300 can vary from about 5 mm to 10 mm, for example in 1 mm increments. Two, three or more lengths can be provided, such as 12, 14 or 16 mm. Two, three or more widths or depths can also be provided, such as 14 and 16 mm.

In one exemplary embodiment, the ACDF cage structure has a width of about 14 mm, a length of about 16 mm, a minimum height of 4.4 mm, a maximum height of 6.3 mm, and a lordosis angle of 8 degrees. The joists have a width of 2.5 mm and a thickness of 0.75 mm. The struts 1310 have a diameter of 2.5 mm.

In an exemplary embodiment, the enveloping volume of the ACDF cage is between about 1,100 $mm^3$ to about 1,700 $mm^3$, such as about 1,411 $mm^3$. The net enveloping volume is between about 900 $mm^3$ to 1,500 $mm^3$, such as about 1,198 $mm^3$.

The material volume of the ACDF cage structure is between about 200 $mm^3$ to about 300 $mm^3$, such as about 248 $mm^3$. The void volume is between about 900 $mm^3$ to about 1,400 $mm^3$, such as about 1,1163 $mm^3$. The net void volume is between about 700 $mm^3$ to about 1200 $mm^3$, such as about 950 $mm^3$.

The ratio of the void volume to the enveloping volume is preferably between about 0.7 to about 0.9, such as about 0.82. The ratio of the net void volume to the net enveloping volume is preferably about 0.73 to about 0.87, such as about 0.79 (e.g 950 $mm^3$:1198 $mm^3$).

The ratio of the void volume to the material volume of the ACDF cage structure is preferably between about 4.2 to about 5.2, such as about 4.69 (e.g 1,163 $mm^3$:248 $mm^3$). The ratio of the net void volume to the material volume is between about 3.3 to about 4.3, such as about 3.83 (e.g 950 $mm^3$:248 $mm^3$). These void volume ratios are much higher than the ratios found in conventional ACDF cages, and provide the advantages discussed herein.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A transforaminal lumbar interbody fusion (TLIF) cage implant device for interbody fusion of lumbar vertebrae comprising:
   a unibody cage structure having an enveloping cage volume and a minimized material volume, the cage structure comprising
   a first and a second generally planar ring member, each ring member formed from an opposing pair of lengthwise joists and an opposing pair of cross joists, the cross joists curved such that each ring member has a substantially race-track configuration, the joists together forming a large opening through the ring member,
   a pair of vertical struts sandwiched between the opposing lengthwise joists of each ring member to further distribute load,
   the ring members fixedly sandwiched on a pair of support members, the support members holding the ring members in a spaced apart relationship to thereby provide a large void volume relative to the enveloping cage volume to thereby allow for receipt of a large volume of bone graft within the cage structure,
   the support members comprising
      a base member on a posterior end of the ring members and
      an arrangement of arcuate struts on an anterior end of the ring members, the arrangement of arcuate struts having an X-shape,
   the ring members positioned on opposing lateral sides of the cage, such that one of the lengthwise joists of each ring member serves as a superior loading surface, the other of the lengthwise joists of each ring member serves as an inferior loading surface, and the cross joists are configured to distribute load between opposing lengthwise joists,
   wherein a ratio of the void volume to the enveloping cage volume is between about 0.7 to about 0.9.

2. The device of claim 1, wherein the ratio of the void volume to the enveloping cage volume is between about 0.79 to about 0.81.

3. The device of claim 1, wherein a ratio of the void volume to the material volume is between about 3.9 to about 4.1.

4. The device of claim 1, wherein the joists are between about 1.5 to about 2.5 mm in diameter.

5. The device of claim 1, wherein each of the vertical struts has an outer diameter of between about 1.5 mm to about 2.5 mm.

* * * * *